United States Patent [19]
McLaughlin et al.

[11] Patent Number: 5,407,665
[45] Date of Patent: Apr. 18, 1995

[54] ETHANOL SUBSTITUTES

[75] Inventors: Kevin T. McLaughlin; William G. Hall, both of Cincinnati, Ohio

[73] Assignee: The Procter & Gamble Company, Cincinnati, Ohio

[21] Appl. No.: 171,502

[22] Filed: Dec. 22, 1993

[51] Int. Cl.⁶ .......................... A61K 7/16; A61K 7/26
[52] U.S. Cl. ........................................ 424/58; 424/49; 426/651
[58] Field of Search .................................. 424/49–58

[56] References Cited

U.S. PATENT DOCUMENTS

| | | | |
|---|---|---|---|
| 3,761,429 | 9/1973 | Yamano et al. | 252/547 |
| 3,992,519 | 11/1976 | Hofmann et al. | 424/49 |
| 4,136,163 | 1/1979 | Watson et al. | 424/54 |
| 4,137,305 | 1/1979 | Rowsell et al. | 424/54 |
| 4,230,688 | 10/1980 | Rowsell et al. | 424/45 |
| 4,357,315 | 11/1982 | Boden | 424/49 |
| 4,357,316 | 11/1982 | Boden | 424/49 |
| 4,459,425 | 7/1984 | Amano et al. | 568/666 |
| 4,726,943 | 2/1988 | Klueppel et al. | 424/54 |
| 4,797,231 | 1/1989 | Schumann et al. | 252/347 |
| 4,876,035 | 10/1989 | Breitzke et al. | 252/550 |
| 4,894,220 | 1/1990 | Nabi et al. | 424/52 |
| 4,906,488 | 3/1990 | Pera | 426/573 |
| 5,214,027 | 5/1993 | Ishihara et al. | 512/10 |

FOREIGN PATENT DOCUMENTS

WO9229319  11/1992  WIPO .............................. A61K 7/00

OTHER PUBLICATIONS

Arctander (1969)"Perfume and Flavor Chemicals", entries for Ethyl Acetate 0137) 1220 1221 1222 1223 1224: Ethyleneglycol. . . Ethers.

Derwent Abstract of Bernard et al WO/PCT92/20319 Nov. 26, 1992.

Derwent Abstract of Lion Corp JPN 59029613 Feb. 16, 1984.

Perfume and Flavor Chemicals, Arctander (1969).

*Primary Examiner*—Shep K. Rose
*Attorney, Agent, or Firm*—David K. Dabbiere; Douglas C. Mohl; Jacobus C. Rasser

[57] ABSTRACT

A composition providing the physiologic sensations of ethanol, comprising an alkoxy glycol ether and preferably further comprising a cooling agent and an oral care or pharmaceutical active.

9 Claims, No Drawings

ETHANOL SUBSTITUTES

TECHNICAL FIELD

The present invention relates to compositions which provide the physiologic sensations of ethanol and which are suitable for use in, e.g., mouthrinse, pharmaceutical, or topical preparations.

BACKGROUND OF THE INVENTION

Ethanol is a choice ingredient, inter alia, in view of its solvent, astringent, and antiseptic properties for use in foods, pharmaceuticals or chemicals and, therefore, is of invaluable worth to the industrial community.

While most of the ethanol produced worldwide is used in the manufacture of various alcoholic beverages, as already suggested, ethanol is quite popular amongst the scientific and industrial communities as well. Used systemically, ethanol is a notable CNS depressant. In its denatured form, ethanol is used externally as an antiseptic, rubifacient and/or astringent. Similarly, industrial chemists use ethanol, principally in its denatured form, for its solvent properties or as an industrial fuel.

Another important reason for ethanol's continued importance as an industrial ingredient stems from its use in topical preparations and relates to the sensory attributes associated with its efficacy. These attributes are most commonly experienced when ethanol is used in the form of a rubbing alcohol, a mouthrinse, or a cough syrup. The primary sensory attributes ascribed to ethanol may be described with respect to the perceived location of the sensation. Topical sensations experienced, e.g., in the oral cavity (or upon skin) include those described as a bite/burn(ing), numbness, and tingling type of sensation while those shared by the nasal cavity are perceived as a sweet, aromatic, and cooling type of sensation.

Considering the commercial importance of compositions which tend to signal efficacy (actual and/or perceived), the advantages to developing compositions which add such a commercially appealing dimension become obvious.

The present inventors have unexpectedly discovered such a composition. Specifically, they have discovered a composition comprising a number of distinct compounds combined in such a way so as to provide the sensory attributes of ethanol without actually incorporating ethanol.

It is, therefore, an object of the present invention to provide a compositions which provide physiologic sensations similar to ethanol. It is further an object of the present invention to provide an ethanol substitute suitable for use in oral compositions such as mouthrinses, pharmaceutical compositions, and in other topical skin care compositions such as cosmetics, lotions and the like. Still a further object of the present invention is to provide compositions which when combined with suitable pharmacologic actives reduce and/or abate plaque, gingivitis, and symptoms associated with respiratory disorders, gastrointestinal disorders, and allergies.

SUMMARY OF THE INVENTION

The present invention relates to a composition which provides physiologic sensations similar to ethanol. The composition comprises:
  a) an alkoxy or glycol ether; and
  b) ethyl acetate; in a ratio of alkoxy or glycol ether to ethyl acetate from about 50 to 1 to about 1000 to 1.

The composition preferably further comprises a cooling agent.

The invention still further relates to cosmetic and pharmaceutical compositions useful in treating, e.g., plaque and/or gingivitis, respiratory disorders, gastrointestinal disorders and allergies; comprising the administration of a safe and effective amount of the compositions of the present invention.

All percentages and ratios herein are by weight unless otherwise specified. Additionally, all measurements are made at 25° C. unless otherwise specified.

By "physiologic sensations" as used herein, include those sensations discerned upon topical administration of ethanol and described as a bite/burn(ing), numbness, tingling, and cooling type of mucosal/skin sensation, a sweet, aromatic type of olfactory sensation, and a bitter-/astringent type of taste sensation. By "safe and effective amount," as used herein, is an amount that is effective to mitigate and/or treat the symptoms for which the active ingredient is indicated in a human without undue adverse side effects commensurate with a reasonable risk/benefit ratio.

DETAILED DESCRIPTION OF THE INVENTION

Those components essential and optional to the present invention are described below.

Essential Components

Alkoxy or Glycol Ethers

Alkoxy or glycol ethers are represented by the general formula:

$ROCH_2CR'HOR$ where R is H-, phenyl group, or an alkyl group of between 1 and 4 carbons and R' is H- or OH-. The alkoxy or glycol ethers useful to the present invention include those ethers formed by alkoxy addition to epoxides. Alkoxy or glycol ethers preferred for use in the present invention are selected from the group consisting of 2-phenoxyethanol, 2-butoxyethanol, 2-ethoxyethanol, or 2-phenoxypropanol. Moreover, mixtures of these compounds may also be use in the compositions of the present invention.

Without being limited to theory, the alkoxy or glycol ethers are believed to provide more of the burn/bite component useful in imitating ethanol's overall effect. Alkoxy or glycol ethers are further described in Remington's Pharmaceutical Sciences, pp. 1313–1314, (Alfonso R. Gennaro, editor) (18th ed. 1990) and under representative compounds in Hawley's Condensed Chemical Dictionary, pp. 489–490, 971, (Revised by Richard J. Lewis, Sr.) (12th ed. 1993), both of which are herein incorporated by reference.

When used in a pharmaceuticcal or skin care composition, the alkoxy or glycol ethers are present at a level form about 0.1% to about 5%.

Ethyl Acetate

Ethyl Acetate, which is represented by the formula:

$CH_3COOC_2H_5$ is widely used commercially as a flavoring agent. It is also used industrially to provide artificial fruit essences and, further, as a solvent for a variety of organic compounds, particularly nitrocellulose varnishes and lacquers. Without being limited by theory, ethyl acetate is believed to provide more of the aromatic/burn(ing) component useful in imitating ethanol's overall effect. Ethyl Acetate is further described in *Hawley's Condensed Chemical Dictionary*, pp. 970–971, (Revised by Richard J. Lewis, Sr.) (12*th* ed. 1993), which is herein incorporated by reference.

When used in a pharmaceutical and skin care composition, ethyl acetate is present in the composition at a level from about 25 ppm to about 75 ppm, preferably within the range from about 30 ppm to about 70 ppm.

Optional Components

Cooling Agents

The present invention may further comprise a cooling agent or a combination of cooling agents. Cooling agents are compounds which directly effect those nerve endings responsible for hot or cold sensations. Suitable cooling agents are menthol, menthol-based or acyclic carboximides, and menthol-based or acyclic ketals (acetals). The cooling agents particularly preferred for use in the present invention are those selected from the group consisting of 3-1-menthoxy propane-1,2-diol, N-substituted-p-menthane-3-carboxamides and acyclic carboxamides and mixtures thereof. While not to be limited by theory, it is believed that the coolant element of the invention provides more of the bite, cooling, numbness and tingling component useful in imitating ethanol's overall effect.

3-1-menthoxy propane 1,2-diol is fully described in detail in U.S. Pat. 4,459,425, issued Jul. 10, 1984 to Amano et. al, incorporated herein by reference in its entirety. This volatile aromatic is commercially available, as TK-10 from Takasago Perfumery Co., Ltd., Tokyo, Japan.

The N-substituted-p-menthane-3-carboxamides are fully described in U.S. Pat. 4,136,163 to Watson et al., issued Jan. 23, 1979 incorporated herein by reference in its entirety. The most preferred cooling agent of this class is N-ethyl-p-menthane-3-carboxamide which is commercially available as WS-3 from Wilkinson Sword Limited.

Useful acyclic carboxamides are fully described in U.S. Pat. 4,230,688 to Rowsell et al., issued Oct. 28, 1980 incorporated herein by reference in its entirety. The most preferred cooling agent of this class is N,2,3-trimethyl-2-isopropylbutanamide which is commercially available as WS-23 from Wilkinson Sword Limited.

Preferred for use herein is a mixture of 3-1-menthoxy propane 1,2-diol, N-ethyl-p-menthane-3-carboxamide and N,2,3-trimethyl-2-isopropylbutanamide in a ratio of 1:75:42, respectively.

These cooling agents are present at a ratio of alkoxy or glycol ether to cooling agent from about 2 to 1 to about 1000 to 1 and when used in a pharmaceutical or skin care composition, at a level of from about 0.01% to about 1%, preferably at from about 0.01% to about 0.4%.

Oral Care Actives

Oral care actives useful to the present invention include those providing effective antiplaque, antibacterial, antitartar, and/or abrasive activity.

Suitable antiplaque agents include proteolytic or glycolytic enzymes, nonionic, anionic, or amphoteric surfactants, and various stannous ion salts are disclosed in U.S. Pat. 4,986,981 to Glace et al., U.S. Pat. 5,041,236 to Carpenter et al., U.S. Pat. 5,180,577 to Polefka et al. and U.S. Pat. 5,145,666 to Lukacovic et al., all of which are herein incorporated by reference.

Suitable antibacterial agents include the quaternary ammonium salts, bisbiguanide salts, triclosan, thymol, cetylpyridinium, tetradecylpyridinium and hexetidine are disclosed in U.S. Pat. 5,176,901 to gallopo et al., U.S. Pat. 4,656,031 to Lane et al., and U.S. Pat. 4,894,220 to Nabi et al., all of which are herein incorporated by reference.

Antitartar (or anticalculus) agents are able to complex calcium found in the mixed matrix layers of plaque. This facilitates the loosening of plaque. Suitable antitartar agents include citric acid/alkali metal titrate combinations along with the various soluble pyrophosphate salts. Pyrophosphates are further described in Kirk & Othmer, *Encyclopedia of Chemical Technology*, 2*nd* ed., vol. 15, Interscience Publishers (1968) and in U.S. Pat. 5,180,576, both herein incorporated by reference.

Abrasives are those compounds used in abrading grinding and polishing teeth. Typical dentally acceptable abrasives include insoluble calcium salts, alumina, silica, synthetic resins and mixtures thereof. U.S. Pat. 4,623,536 discloses sodium bicarbonate, baking soda, as a mild abrasive and is herein incorporated by reference. Other compounds useful as abrasives are described in U.S. Pat. 5,176,901 herein incorporated by reference.

Pharmaceutical Agents

The pharmaceutical actives of the present invention may be selected from among the various groups of chemical compounds or materials suitable for oral administration and having a pharmacological action. These pharmaceutically active compounds or materials should be compatible with the other essential ingredients and compatible in combination with other included active materials or compounds. The pharmaceutically active compounds or materials are present at a level from about 0.01% to about 75%, preferably from about 0.1% to about 50%, more preferably from about 1.0% to about 25% and most preferably from about 1.0% to about 10%. The pharmaceutically active materials or compounds may include, but are not limited to: bronchodilators, anorexiants, antihistamines, nutritional supplements (such as vitamins, minerals, fatty acids, amino acids, and the like), laxatives, analgesics, antacids, $H_2$-receptor antagonists, antidiarrheals, decongestants, antitussives, antinauseants, antibacterials, antifungals, antivirals, expectorants, anti-inflammatory agents, antipyretics vitamins and pharmaceutically acceptable salts and mixtures thereof.

The term "pharmaceutically acceptable salts" refers to salts prepared from pharmaceutically acceptable non-toxic bases including inorganic bases and organic bases. Salts derived from inorganic bases include sodium, potassium, lithium, ammonia, calcium, magnesium, ferrous, zinc, manganous, aluminum, ferric, manganic salts and the like. Salts derived from pharmaceutically acceptable organic non-toxic bases include salts of primary, secondary, tertiary and quaternary amines, substituted amines including naturally occurring substituted amines, cyclic amines and basic ion exchange resins, such as triethylamine, tripropylamine, 2-dimethylaminoethanol, 2diethylaminoethanol, lysine, arginine, histidine, caffeine, procaine, N-ethylpiperidine, hydrabamine, choline, betaine, ethylenediamine, glucosamine, methylglycamine, theobromine, purines, piperazine, piperidine, polyamine resins and the like.

Examples of useful decongestants include pseudoephedrine, phenylpropanolamine, phenylephrine and ephedrine, their pharmaceutically acceptable salts, and mixtures thereof.

Examples of useful antitussives include dextromethorphan, chlopedianol, carbetapentane, caramiphen, noscapine, diphenhydramine, codeine, hydrocodone, hydromorphone, their pharmaceutically acceptable salts, and mixtures thereof.

Examples of useful expectorants (also known as mucolytic agents) include; glyceryl guaiacolate, terpin hydrate, ammonium chloride, N-acetylcysteine, and ambroxol, their pharmaceutically acceptable salts, and mixtures thereof.

Examples of useful analgesics include; morphine, codeine, meperidine, pentazocine, propoxyphene, acetaminophen, allopurinol, acetylsalicylic acid, choline salicylate, ketoprofen, magnesium silicate, salsalate, fenoprofen, ibuprofen, indomethacin, naproxen, and many others and their pharmaceutically acceptable salts and mixtures thereof.

Analgesics, decongestants, expectorants and antitussives, as well as their acceptable dosage ranges are described in U.S. Pat. 4,783,465 to Sunshine et al., issued Nov. 8, 1988, and U.S. Pat. 4,619,934 to Sunshine et al., issued Oct. 28, 1986, which are incorporated by reference herein.

Examples of useful antihistamines include; brompheniramine, chlorpheniramine, clemastine, dexchlorpheniramine, diphenhydramine, doxylamine, promethazine, terfenadine, triprolidine and many others and their pharmaceutically acceptable salts and mixtures thereof.

Examples of useful gastrointestinal agents include; anticholinergics, including atropine, clidinium and dicyclomine; antacids, including aluminum hydroxide, bismuth subsalicylate, calcium carbonate and magaldrate; $H_2$-receptor antagonists including: cimetidine, famotidine, nizatidine and ranitidine; laxatives, including: phenolphthalein and casanthrol; and antidiarrheals including: diphenoxylate and loperamide.

Further examples of suitable analgesics, decongestants, antitussives, expectorants and antihistamines as well as bronchodilators, anorexiants, laxatives, antiemetics, antibacterials, antimicrobials, antifungals, antiinflammatory agents, antivirals, antipyretics, nutritional supplements, anticholinergics, antacids, $H_2$-receptor antagonists, antidiarrheals and other miscellaneous gastrointestinal compounds and their acceptable dosage ranges are described in *Remington's Pharmaceutical Sciences*, pp. 734–789, 791–799, 861–868, 907–945, 875–888, 1002–1034, 1098–1121, 1124–1131, 1173–1224, 1232–1241, (Alfonso R. Gennaro, editor) (18th ed. 1990), herein incorporated by reference.

Solvents or Solvent System

Another essential ingredient of the composition of the present invention is a solvent or solvent system such as those described in U.S. Pat. 5,141,961, Aug. 25, 1992 to Coapman, herein incorporated by reference. The solvent(s), which constitute the bulk of the present composition act as a carrier for the flavoring oils. The solvent or solvent system solubilizes the flavoring oils in the concentrate and aids in dispersing, the oil soluble components of the concentrated formulation thereby forming a uniformly dispersed mixture. The solvents most preferred for use in the present invention are: propylene glycol and polyethylene glycols or mixtures thereof. Propylene glycol and polyethylene glycols being most preferred.

Propylene glycol is well known in the art and available from any of a number of suppliers. Propylene glycol is miscible in all proportions with water and also has the ability to dissolve the flavoring agent(s) of the present invention. Propylene glycol suitable for use in the present invention is obtainable from any number of sources such as Dow Chemical. Polyethylene glycols are also well known in the art and lower molecular weight species possess characteristics similar to propylene glycol. Polyethylene glycols suitable for use in the present invention are the polyethylene glycols having an average molecular weight of less than or equal to 600, such as PEG300 "Carbowax" supplied by Union Carbide.

Solvents comprise from about 30% to about 85%, preferably from about 35% to about 75% and most preferably from about 45% to about 60% of the concentrated form of the mouthrinse.

Water

Water is present in the concentrated composition of the present invention. Water comprises from about 10% to about 40%, preferably from about 18% to about 30% and most preferably from about 22% to about 26% of the oral compositions described herein. These amounts of water include the free water which is added, plus that amount which is introduced with other materials such as with sorbitol. The water, used in the present invention should preferably be deionized, distilled, free of organic impurities and bacteria and substantially free of metal ions.

Pharmaceutical Carriers

The compositions in which the present composition finds application are principally topical. These topical compositions include not only compositions such as dentifrices, mouthwashes, and gargles, but also compositions applied to, or which, in normal usage, come in contact with other internal mucous membranes of the body, such as those of the nose, mouth, or throat, regardless of whether that application is direct or indirect or via inhalation. These compositions find further applicability to the external surfaces of the human body—whether for medical or other reasons—as, for example, perfumes or powders as well as other skin care compositions, such as lotions, liniments, oils and ointments. Also included within the compositions of the present invention are articles such as cleansing tissues and toothpicks impregnated or coated with the active cooling compound.

In formulating the compositions of the present invention, the ethanol imitating composition will usually be incorporated into a carrier which may be completely inert or contain other active ingredients. A wide variety of carriers may be used, depending upon the end use of the composition, such carriers including solids, liquids, emulsions, foams and gels. Typical carriers include aqueous solutions; oils and fats such as hydrocarbon oils, fatty acid esters, long chain alcohols and silicone oils; finely divided solids such as starch or talc; cellulosic materials such as paper tissue; low-boiling hydrocarbons and halohydrocarbons used as aerosol propellants; gums and natural or synthetic resins.

The following illustrates the range of compositions into which the present composition can be incorporated:

1. Oral hygiene compositions including mouthwashes, toothpastes, tooth-powders, prophylaxis pastes, lozenges, and gums providing antiplaque, antibacterial, antitartar, and/or abrasive activity.
2. Topical skin care compositions including after shave lotions, shaving soaps, creams and foams, water, deodorants and antiperspirants, "solid colognes", soaps, bath oils and salts, shampoos, hair oils, talcum powders, face creams, hand creams, sunburn lotions, cleansing tissues, toothpicks, hair tonics, eyedrops.

3. Medicaments including antiseptic ointments, liniments, lotions, decongestants, counter-irritants, cough mixtures, throat lozenges, indigestion preparations, oral analgesics, allergy products.

4. Miscellaneous compositions such as water soluble adhesive compositions for envelopes, postage stamps, adhesive labels etc.

Particular preparations according to the invention are discussed in more detail below.

Oral Hygiene Compositions:

Because of the cooling, tingling and biting sensations imparted to the mouth, the present composition is particularly useful in oral care products at a level of from about 0.35% to about 1.0%. Suitable oral care products would be those products including mouthwashes, toothpastes, toothpowders, prophylaxis pastes, lozenges, and gums providing antiplaque, antibacterial, antitartar, and/or abrasive activity.

Topical skin Care Compositions:

Because of the ethanol imitating sensations imparted to the skin, a major utility of the present invention will be in a wide range of skin care preparations and articles. The particular preparations discussed below are to be taken as exemplary.

These compositions are especially useful in shaving lotions, water etc., where the compounds are in aqueous solutions, such solutions will usually also contain perfumes or mild antiseptics or both.

Another field of utility will be in soaps, shampoos, bath oils etc. where the compounds will be used in combination with an oil or fat or a natural or synthetic surfactant e.g. a fatty acid salt or a lauryl sulphate salt, the composition usually also containing an essential oil or perfume. The range of soap compositions will include soaps of all kinds e.g. skin care soaps, shaving soaps, shaving foams etc.

A further class of skin care compositions into which the compounds may be incorporated includes cosmetic creams and emollients, such creams and emollients usually comprising a base emulsion and optionally a range of ingredients such as wax, preservative, perfume, antiseptics, astringents, pigments etc. Also included within this class are lipstick compositions, such compositions usually comprising an oil and wax base into which the compounds can be incorporated along with the conventional ingredients, i.e. pigments, perfumes etc. Once again the formulation of such compositions is conventional.

Medicaments:

In addition to the present composition's cooling, tingling and biting effect on the mucous membranes of the mouth, it produces similar effects on the skin, throat, nose and gastrointestinal tract, making it useful in combination with a variety of pharmaceutical actives. These compositions may take the form of oral, nasal, throat spray and/or topical pharmaceutical compositions.

Certain compositions of this invention are illustrated by the following nonlimiting examples. These examples are strictly given for illustration purposes.

EXAMPLES

The following examples further describe and demonstrate embodiments within the scope of the present invention. The examples are given solely for the purpose of illustration and are not to be construed as limitations of the present invention, as many variations are possible without departing from the spirit and scope of the invention.

EXAMPLE I

A mouthwash composition is made by combining the following components.

| Ingredients | W/V % |
| --- | --- |
| propylene glycol | 10.0000 |
| flavor | 0.1750 |
| polysorbate-80 | 0.0500 |
| poloxamer-407 | 0.2000 |
| 2-phenoxyethanol | 0.5000 |
| 3-1-menthoxypropane 1,2-diol[1] | 0.0555 |
| N-ethyl-p-menthane-3-carboxamide[2] | 0.0225 |
| N,2,3-trimethyl-2-isopropylbutanamid[3] | 0.0125 |
| ethyl acetate | 0.0050 |
| sodium saccharin | 0.0540 |
| sodium benzoate | 0.0540 |
| glycerin, USP | 10.0000 |
| benzoic acid | 0.0045 |
| blue dye No. 1, 1.00% solution | 0.0300 |
| yellow dye No. 5, 1.00% solution | 0.0300 |
| purified water | q.s. to 100 |

[1]Available as TK-10 supplied by Takasago Perfumery Co.
[2]Available as WS-3 supplied by Sterling Organics.
[3]Available as WS-23 supplied by Wilkinson Sword Limited.

In a stainless steel or glass mixing tank containing the quantity of solvent, sequentially add the following ingredients dissolving each with agitation: alkoxy or glycol ether, ethyl acetate, cooling agent, antibacterial, humectant(s), purified water, and dye.

EXAMPLE II

An aftershave composition is made by combining the following components using conventional mixing technology as described in Example I.

| Ingredients | W/V % |
| --- | --- |
| Non-alcohol Fragrance | 1.500 |
| Hexylene Glycol | 37.500 |
| 2-phenoxyethanol | 3.360 |
| Ethyl acetate | 0.032 |
| 3-1-menthoxypropane 1,2-diol | 0.376 |
| N-ethyl-p-menthane-3-carboxamide | 0.152 |
| N,2,3-trimethyl-2-isopropylbutanamid | 0.080 |
| Water | Q.S. to 100% |

EXAMPLE III

A pharmaceutical composition is made by combining the following components using conventional mixing technology as described in Example I.

| Ingredients | W/V % |
| --- | --- |
| Acetaminophen | 3.33333 |
| Doxylamine Succinate | 0.04166 |
| Pseudoephedrine HCl | 0.20000 |
| Dextromethorphan HBr | 0.10000 |
| Sodium Citrate, Hydrous | 1.00000 |
| Sugar Liquid #1 | 65.00000 |
| Sodium Saccharin | 0.07000 |
| Citric Acid, Anhydrous | 0.22856 |
| Glycerin | 5.00000 |
| Propylene Glycol | 15.00000 |
| Polyethylene Glycol 400 | 5.00000 |
| Anethol | 0.01483 |
| Green Shade CSL-15689 | 0.00500 |

-continued

| Ingredients | W/V % |
| --- | --- |
| 2-phenoxyethanol | 0.33600 |
| Ethyl acetate | 0.00320 |
| 3-1-menthoxypropane 1,2-diol | 0.03760 |
| N-ethyl-p-menthane-3-carboxamide | 0.01520 |
| N,2,3-trimethyl-2-isopropylbutanamid | 0.00800 |
| Water | Q.S. to 100% |

What is claimed:

1. A mouthwash composition which contains less than about 10% ethanol and provides physiologic sensations of bite, cooling, numbness, and tingling similar to ethanol, comprising:
   a) an alkoxy or glycol ether; and
   b) ethyl acetate; in a ratio of from about 100 to 1 to about 1000 to 1 in an aqueous mouthwash formulation containing a flavor oil dispersed in a solvent system effective to solubilize said flavor oil.

2. A composition according to claim 1 which further comprises a cooling agent in a ratio of alkoxy or glycol ether:cooling agent of from about 2 to 1 to about 1000 to 1, respectively.

3. A composition according to claim 2 wherein the alkoxy or glycol ether is selected from the group consisting of 2-phenoxyethanol, 2-butoxyethanol, 2-ethoxyethanol, or 2-phenoxypropanol.

4. A composition according to claim 3 wherein the preferred alkoxy or glycol ether is 2-phenoxyethanol.

5. A composition according to claim 4 wherein the Coolant agent is selected from the group consisting of: 3-1-methoxypropane 1,2-diol, N-ethyl-p-methane-3-carboxamides, and acyclic carbamides and mixtures thereof.

6. A composition according to claim 5 wherein the ratio alkoxy or glycol ether to Coolant is from about 2 to 1 to about 1000 to 1.

7. A mouthrinse carrier according to claim 6 which further comprises an active ingredient having antibacterial activity.

8. A mouthrinse carrier according to claim 7 which further comprises an active ingredient having antitartar activity.

9. A method of treating plaque and/or gingivitis which comprises rinsing the oral cavity with a safe and effective amount of the composition according to claim 7.

* * * * *